United States Patent [19]

Gutierrez et al.

[11] Patent Number: 4,702,850

[45] Date of Patent: Oct. 27, 1987

[54] POWER TRANSMITTING FLUIDS CONTAINING ESTERS OF HYDROCARBYL SUCCINIC ACID OR ANHYDRIDE WITH THIO-BIS-ALKANOLS

[75] Inventors: Antonio Gutierrez, Mercerville; Stanley J. Brois, Westfield; Jack Ryer, East Brunswick; Harold E. Deen, Cranford, all of N.J.

[73] Assignee: Exxon Research & Engineering Co., Florham Park, N.J.

[21] Appl. No.: 886,304

[22] Filed: Jul. 16, 1986

Related U.S. Application Data

[63] Continuation of Ser. No. 359,801, Mar. 19, 1982, abandoned, which is a continuation-in-part of Ser. No. 194,067, Oct. 6, 1980, abandoned.

[51] Int. Cl.$^4$ ........................................... C10M 135/24
[52] U.S. Cl. .................................. 252/48.2; 252/560; 252/395; 252/396
[58] Field of Search ............... 252/48.2, 56 D, 395, 252/396; 560/195

[56] References Cited

U.S. PATENT DOCUMENTS

| | | |
|---|---|---|
| 2,540,570 | 2/1951 | Cyphers ................................ 252/ |
| 2,561,232 | 7/1951 | Rudel ................................... 260/ |
| 3,045,042 | 7/1962 | Staker ............................. 252/56 |
| 3,117,091 | 1/1964 | Staker ............................. 252/56 |
| 3,198,737 | 8/1965 | Calhoun .............................. 252/ |
| 3,278,566 | 10/1966 | Calhoun .............................. 260/ |
| 3,381,022 | 4/1968 | LeSuer ................................ 260/ |
| 3,556,997 | 1/1971 | Leister ................................ 252/ |
| 3,576,846 | 4/1971 | Leister ................................ 260/ |
| 3,933,659 | 1/1976 | Lyle et al. .......................... 252/ |
| 4,105,571 | 8/1978 | Shaub et al. ........................ 252/ |
| 4,176,074 | 11/1979 | Coupland et al. .................. 252/ |

FOREIGN PATENT DOCUMENTS

978161  12/1964  United Kingdom .

*Primary Examiner*—Jacqueline V. Howard
*Attorney, Agent, or Firm*—J. J. Mahon; R. A. Maggio

[57] ABSTRACT

Mineral oil based power transmitting fluids, such as automatic transmission fluids, are disclosed which contain 0.05 to 2.0 weight percent of an ester of a thio-bis alkanol and a $C_{12}$–$C_{50}$ hydrocarbon succinic acid or anhydride, the ester being a multifunctional additive providing the properties of friction modification, corrosion inhibition, anti-wear, oxidation inhibition and extreme pressure properties to the fluids.

10 Claims, No Drawings

POWER TRANSMITTING FLUIDS CONTAINING ESTERS OF HYDROCARBYL SUCCINIC ACID OR ANHYDRIDE WITH THIO-BIS-ALKANOLS

This application is a continuation of U.S. Ser. No. 359,801, filed Mar. 19, 1982, which is a continuation-in part of application Ser. No. 194,067, filed Oct. 6, 1980, both now abandoned.

The present invention relates to functional fluid compositions containing ester additives derived from hydrocarbon substituted succinic acid or anhydride which function as multi-purpose additives thereby providing to functional fluid or power transmitting oleaginous compositions, such as hydraulic fluids, automatic transmission fluids (ATF) and a number of desirable properties.

More particularly, the invention relates to the use of mono- and di-esters of thio-bis alkanols and alkenyl succinic acid or anhydrides which are especially effective as friction modifier additives, anti-wear additives and corrosion inhibitors in power transmission fluids.

The prior art contains a wide variety of compounds useful for friction modification in lubricating oils and in ATF. Representative disclosures are U.S. Pat. No. 3,933,659 which discloses fatty acid ester and amides as friction modifiers for functional fluids; U.S. Pat. No. 4,176,074 describes molybdenum complexes of polyisobutenyl succinic anhydride-amino alkanols as friction modifiers; U.S. Pat. No. 4,105,571 discloses glycerol esters of dimerized fatty acids as friction modifiers in lubricating oils.

Diesters of monohydric alcohols, including those with sulfur linkages, which have been esterified with $C_3$-$C_{24}$ alkenyl succinic acid are disclosed in U.S. Pat. No. 2,561,232. The diesters disclosed therein are said to be useful as synthetic lubricant fluids. U.S. Pat. Nos. 3,198,737 and 3,278,566 disclose fatty esters of thioglycols and other diols useful as intermediates in the preparation of polysulfoxyl esters having utility as extreme pressure agents. U.S. Pat. No. 2,540,570 discloses glycol esters of rosin or other fatty acids with thioglycols, the comppounds being useful as extreme pressure additives.

U.S. Pat. Nos. 3,045,042 and 3,117,091 both disclose partial esters of alkenyl succinic anhydride with a variety of polyhydric alcohols such as 2,2'-thiodiethanol as rust preventative additives in petroleum fractions such as gasoline and other fuels. U.S. Pat. Nos. 3,576,846 and 3,556,997 disclose sulfinyl-containing alkenyl succinates useful as dispersants, corrosion inhibitors and anti-wear agents in lubricating oil and fuel compositions. U.S. Pat. No. 3,381,022 generally discloses esters of $C_{50}$ and higher hydrocarbon succinic acids suitable as additives in oils and fuels as well as being suitable plasticizers, detergents and emulsifiers.

In accordance with the present invention, there are provided power transmitting hydrocarbon mineral oil compositions containing effective amounts of mono- or di-esters, and mixtures thereof, formed by the reaction of (a) thio-bis-alkanols of the formula:

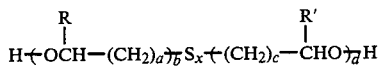

wherein R and R' each independently may be hydrogen, methyl or ethyl, x may be 1–4, a, b, c, and d each independently may be 1–3; with (b) 1 to 2 moles, per mole of the thio-bis-alkanol, of an aliphatic hydrocarbon-substituted succinic acid or anhydride or mixtures thereof wherein the aliphatic hydrocarbon group contains from 12 to 50 carbon atoms.

As used herein, the term "monoester" or "hemiester" refers to product made from equimolar proportions of said thio-bis-alkanol and a succinic acid or anhydride, that is, one free hydroxyl group remains; while the term "di-ester" refers to those products wherein each hydroxyl group of the thio-bis-alkanol is esterified with a hydrocarbyl-substituted or polyolefin-substituted succinic acid or anhydride. In either case, a succinic acid moiety remains, i.e., a —C(O)OH group, but this may be neutralized with metals or amines as described herein below to form useful salt derivatives.

The hydrocarbyl-succinic acids or anhydrides are per se known in the art and the commonly used anhydride may be represented by the formula:

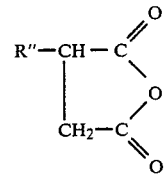

wherein R" is a $C_{12}$-$C_{50}$ aliphatic hydrocarbon group, such as an alkyl, alkenyl, isoalkyl, isoalkenyl or cycloalkyl hydrocarbyl group. Oligomers containing 12 to 50 carbon atoms are also suitable as the aliphatic hydrocarbyl group, such as oligomers of $C_2$-$C_5$ monoolefins, such as isobutene.

The aliphatic hydrocarbyl group may be an unsubstituted hydrocarbon group or it may contain substituents such as chlorine, bromine, sulfur, phosphorus, nitrogen or oxygen which will not affect the utility of the final mono- or di-ester product. A preferred substituent is sulfur as exemplified by 2-octadecylthio succinic anhydride.

These compounds may be prepared by the reaction of maleic anhydride with olefins, oligomeric polyolefins, or with chlorinated derivatives thereof using techniques known in the art. Succinic acids are readily produced by hydrolysis of the corresponding anhydride. Especially preferred in preparing the mono- and di-ester compounds are $C_{18}$-$C_{22}$ alkenyl succinic anhydrides, such as octadecenyl succinic anhydride.

The term thio-bis-alkanol as used herein represents those ester-forming diol compounds of the formula:

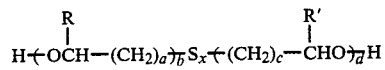

wherein R and R' each independently may be hydrogen, methyl or ethyl, x may be 1–4, a, b, c and d each independently may be 1–3. If b or d are greater than 1, then the formula is meant to express ethoxylated derivatives of such alcohols.

Preferred embodiments are those thio-bis-alkanols within the foregoing formula herein a, b, c and d are each 1 or 2 and R is H or $CH_3$. Specific compounds include 2,2'-dithiodiethanol 2,2'-thiodiethanol, di(2-hydroxypropyl)disulfide and 3,3'-thiodipropanol.

Formation of the mono- and di-esters of the present invention proceeds by reacting the appropriate quantities of anhydride (or acid) and thio-bis-alkanol with or without an inert organic solvent diluent and heating and stirring the mixture at about 50° to 150° C. until esterification of the anhydride is complete. Equimolar quantities of each reactant will provide mainly the mono- (or hemi-) ester and reaction of 2 moles of hydrocarbon substituted succinic acid or anhydride per mole of thio-bis-alkanol will provide the di-ester material. Also, products useful in the present invention encompass mixtures of such mono- and di-esters.

Insofar as yields are concerned, the reaction of an equimolar ratio of thio-bis-alkanol and hydrocarbon succinic anhydride will provide a product containing about 80% mono-ester and about 20% di-ester. The di-ester is produced in somewhat higher yields, about 90% of the product being di-ester and about 10% mono-ester when the mole ratio of succinic anhydride to thio-bis-alkanol is 2:1. The novel di-ester compounds of this invention are particularly preferred embodiments exhibiting generally better thermal and oxidative stability and offering better friction-reducing properties.

In the case of a di-ester compound, it is suitable to use succinic anhydrides having less than $C_{12}$ hydrocarbon substituent so long as the total number of carbon atoms of the hydrocarbon substituents on the succinic moiety of the ester commmpounds is at least $C_{12}$ since oil solubility of the finished compound is the important property. Thus, the invention encompasses the use in power transmitting fluids of symmetrical di-esters based, for example, upon two moles of decenyl succinic anhydride or an asymmetrical di-ester based upon a mole of a $C_3$ hydrocarbon substituted succinic anhydride and a $C_{16}$ hydrocarbon substituted succinic anhydride.

Further embodiments of the present invention are power transmitting fluids containing the borated derivatives of the mono-ester compound, as well as metal and amine salts of either the mono- or di-ester, formed by reaction with the free succinic acid moiety which is present in either the mono- or di-ester of this invention.

Borated derivatives are based upon a reaction with the free hydroxyl group of the mono-ester and the boration technique is known in the art and is carried out by adding from about 1 to 3 weight percent, based on the weight of mono-ester, or boron oxide, boron halide, boron acid or boron acid ester to the mono-ester as a slurry in mineral oil and heating with stirring from about 135° C. to 165° C. followed by nitrogen stripping and filtration of the product. The borated product will generally contain about 0.1 to 2.0, preferably 0.2 to 9.8 weight percent boron based upon the total weight of borated mono-ester.

The metal salts of the mono- and di-esters are preferably the zinc, nickel, copper and molybdenum salts formed by simply reacting a free succinic acid group of the mono- or di-ester with a suitable metal, such as zinc, nickel, copper or molybdenum acetate in the presence of xylene and azeotroping acetic acid. Other suitable metals which can form useful derivatives are calcium, barium and magnesium, which are commonly used for preparation of anti-wear and corrosion inhibition additives. Ammonium salts are also suitable.

Amine salts may be generally based upon an amino or polyamino compound which is reactive toward the free succinic acid moiety. Suitable amines include primary or tertiary secondary hydrocarbyl and aliphatic hydrocarbyl mono- or polyamines having about 1 to 30 carbon atoms, such as methyl and ethyl amine, aniline, diethanolamine, dipropylamine, ethylene diamine, morpholine, phenylene and naphthalene diamines and the like.

The compositions of the present invention will contain the ester compound in amounts effective to provide the desirable properties of friction modification or retention, corrosion inhibition, such as copper and brass corrosion inhibition, wear resistance and extreme pressure properties to the power transmitting fluid. Generally there will be present 0.05 to 2 wt % of the ester based on the total weight of the composition, preferably there is employed about 0.1 to 0.5 wt% of the ester in the hydrocarbon mineral oil fluid such as an automatic transmission fluid which is the preferred composition. Power transmitting fluids of the present invention have the capability, when formulated with the ester additive, for passing a number of critical tests to qualify these fluids for commercially suitable automatic transmission fluids, hydraulic fluids, heavy duty power transmitting fluids and the like. Friction durability and wear resistance are two properties of great significance which are exhibited by the fluid compositions of the present invention.

Since the use of the ester additive provides a number of properties to the fluid, the power transmitting fluids of this invention are multifunctional in nature, since the same ester additive is suitable for passing or exceeding the relevant qualification tests for a number of functional fluids.

The products have been found to be useful generally in power transmitting fluids based on hydrocarbon mineral oils such as automatic transmission fluids, hydraulic fluids, power steering fluids and the like.

The compounds of the present invention are preferably employed in automatic transmission fluids. Such ATF compositions contain a number of conventional additives providing their normal attendant functions and are typically blended into the mineral oil base in the following ranges:

| Components | Concentration Range (Vol. %) |
|---|---|
| V. I. Improver | 1–15 |
| Corrosion Inhibitor | 0.01–1 |
| Oxidation Inhibitor | 0.01–1 |
| Dispersant | 0.5–10 |
| Pour Point Depressant | 0.01–1 |
| Demulsifier | 0.001–0.1 |
| Anti-Foaming Agents | 0.001–0.1 |
| Anti-Wear Agents | 0.001–1 |
| Seal Swellant | 0.1–5 |
| Friction Modifiers | 0.01–1 |
| Mineral Oil Base | Balance |

Typical base oils for automatic transmission and other power transmitting fluids include a wide variety of light hydrocarbon mineral oils, such as, naphthenic base, paraffin base and mixtures thereof, having a lubricating viscosity range of about 34 to 45 SUS (Saybolt Universal Seconds) at 38° C.

The invention is further illustrated by the following examples which are not to be considered as limitative of its scope.

EXAMPLE 1

This example shows the preparation of 6-hydroxy-3,4-dithiahexyl 2-octadecenyl succinic acid ester.

0.2 mole (70 g.) of 2-octadecenyl succinic anhydride and 0.2 mole (30.8 g.) of 2,2-dithiodiethanol were combined and heated gradually to 140° C. The mixture was stirred at this temperature until IR analysis showed the absence of an ahydride carbonyl absorption. Elemental analysis showed 12.2% S; theory for a mono-ester is 12.7% S.

The product of the Example (hereafter referred to as OSA-DBE) was evaluated in a number of tests which indicate its friction reducing, anti-wear and corrosion inhibitor preparation rendering it useful as a multi-purpose additive for ATF and other functional power transmitting fluids.

EXAMPLE 2

The OSA-DBE of Example 1 was evaluated for friction reducing properties in the Ball-On-Cylinder Test which is reported in Publication No. 780599 entitled "Improved Fuel Economy Via Engine Oils" by Waddey et al and published by the Society of Automotive Engineers, Warrendale, PA.

In this test a steel ball ($\frac{1}{2}$" diameter) rubs at 0.26 rpm on a 1-13/16" diameter steel cylinder. Both ball and cylinder are SAE 52100 medium alloy steels except that the ball is hardened. The cylinder is wetted by 30 ml. test oil in a 104° C. heated bath. Test duration is 60 minutes (16 revolutions). The applied load is 4 kg and 2 kg weight with a 2:1 arm ratio is used.

A formulated lubricating oil composition, in accordance with ASTM High Reference Oil Specifications, was prepared containing conventional amounts of an anti-wear additive, overbased metal detergents additive and all-soluble dispersant, with the base stock being a mineral paraffinic oil having a viscosity of 31 cS min. at 37.8° C. This ASTM High Reference Oil Formulation is noted as Formulation A. Formulation B is the same blend with 1.0 wt% of the OSA-DBE of Example 1. The results of a comparative evaluation are in Table 1, which reports the significant cylinder wear-track data from the Ball-On-Cylinder Test. The data shows that the co-efficient of friction was reduced without any increase in the wear track depression of the cylinder.

TABLE I

| WEAR-TRACK RESULTS | | |
|---|---|---|
| | Formulation A | Formulation B |
| Coefficient of Friction | 0.35 | 0.1 |
| Wear (micro inches) | 38 m-inch | 30 m-inch |

EXAMPLE 3—ATF EVALUATIONS (a) An automatic transmission fluid containing a conventional dispersant, anti-oxidant and seal sweller to which was added 0.3 wt% of the OSA-DBE of Example 1 was evaluated pursuant to the General Motors Corp., Chevrolet Turbo Hydramatic Oxidation Test (THM 350) published by General Motors Corp., Detroit, Mich. (Specification GM 6137-M, 2nd Ed., July 1978, Appendix Page 9). The results and the test standards are set forth in Table 2 below. Test conditions were 300 hours at 325° F. (The test evaluates a fluid in a specifically modified transmission under specified conditions.)

| THM 350 TEST | |
|---|---|
| Example 3 Fluid - Results | Standard |
| TAN (Total Acid Number) | |
| ASTM D-664 Increase 5.09 | Increase of 7 orless |
| IR Carbonyl Absorbance 0.442 | Increase of 8 or less |
| Transmission Parts - Clean | Clean |

| -continued | |
|---|---|
| THM 350 TEST | |
| Example 3 Fluid - Results | Standard |
| Cooler Corrosion - Pass | Pass |

(b) The same formulation was evaluated for its friction-reducing properties using the SAE No. 2 Friction Machine and was found effective. This test requires satisfactory operation for 100 hours with no unusual clutch plate wear or composition-faced plate flaking. After the initial 24 hours of operation, dynamic torque must remain between 115 and 175 N.m and static torque must not exceed dynamic torque by more than 14 N.m. Clutch engagement time must remain between 0.45 and 0.75 seconds.

(c) The same formulation was evaluated for corrosion inhibition properties using the Falex Pin Corrosion Test and the results are listed below. The Falex Laboratory Wear Tester uses two "V" blocks clamped against a rotating shaft. The test is described in "Lubricant Testing", E. G. Ellis, Scientific Publications, Ltd., 1953 pages 150-154.

Load = 1,750 lb. to failure
Pin-Wear = 10 mg. (500 lb. load for 30 min.)
Block Wear = 0.1 mg.

(d) Corrosion tests were conducted which comprised immersing copper and brass specimens $3 \times \frac{1}{2} \times 1/6$ inches weighed to 0.1 milligram in 40 cc. of the Example 3 ATF and maintained at 300° F. for 65 hours. Thereafter, the specimens are washed in hexane, rubbed to remove any loose deposits and reweighed. The results were 10 mg. copper loss and 0 mg. brass loss.

Examples 4–9 show the preparation of other compounds useful in the compositions of the invention including di-esters, borated derivatives and metal salt derivatives.

EXAMPLE 4

This example illustrates the preparation of the di-ester of 2-octadecenyl succinic anhydride and 2,2'-dithio-bisethanol. About 150 g (0.43 mole) of 2-octadecenyl succinic anhydride was heated to 140° C. while stirring under nitrogen atmosphere. Then 33 g (0.215 mole) of 2,2'-dithio-di-ethanol were added dropwise for a period of ten minutes. The mixture was stirred at this temperature until IR analysis showed the absence of an anhydride carbonyl absorption. Elemental analysis showed 8.1% sulfur; theory for a bis-hemi-ester is 7.5% S.

EXAMPLE 5

This example shows the preparation of the monoester of 2-octadecenyl succinic anhydride with 2,2'-thio-bis-ethanol.

0.4 mole (140 g) of 2-octadecenyl succinic anhydride and 0.4 mole (48.8 g) of 2,2'-thio-bis-ethanol were combined and heated gradually at 150° C. The mixture was stirred at this temperature for about one half hour. The infrared analysis showed absence of an anhydride carbonyl absorption band. Elemental analysis showed 66.17% C, 10.33% H and 6.79% S, theory for monoester requires 66.05% C, 10.23% H and 6.78% S.

EXAMPLE 6

This example shows the preparation of a di-ester of 2-octadecenyl succinic anhydride with 2,2'-thio-bis-ethanol.

About 636 g (1.81 mole) of 2-octadecenyl succinic anhydride were heated to 150° C. and 111 g (0.91 mole) of 2-2'-thio-bisethanol were added dropwise for a period of one half hour. The mixture was stirred at this temperature for another half hour or until the IR analysis showed the absence of carbonyl anhydride band.

EXAMPLE 7

This example shows the preparation of the di-ester of 2-octadecyl-thio succinic anhydride with 2,2'-dithio-diethanol.

About 57 g (0.15 mole) of 2-octadecylthio succinic anhydride (prepared with the a-dition of 1-octadecyl mercaptan to maleic anhydride, or via the addition of mercapto succinic acid to 1-octadecene) were dissolved in 50 ml of tetrahydrofuran and combined with 11.6 g (0.075 mole) of 2,2'-dithiodiethanol. The THF solution was gradually heated and the THF was distilled off. The residue was heated to 140° C. and kept at this temperature for one half hour. The infrared analysis showed the absence of a carbonyl anhydride absorption band.

EXAMPLE 8

This example shows the preparation of a borated derivative of the mono-ester of 2-octadecenyl succinic anhydride and 2,2'-dithiodiethanol.

0.1 mole (101.2 g) of the hemi-ester (mono-ester) of 2-octadecenyl succinic anhydride and 2,2-dithiodiethanol was combined with 0.1 mole (6.1 g) of boric acid in 100 ml of xylene. The reaction mixture was heated to 140° C. for four hours until water evolution closed. The xylene was distilled off and an oily residue was obtained. The infrared spectrum of the residue showed it to be the desired borated ester.

EXAMPLE 9

This example shows the preparation of the zinc and copper salts of the di-ester of octadecenyl succinic anhydride and 2,2'-dithio-bis-ethanol.

(a) 0.1 mole (85.4 g) of the di-ester of Example 4 was combined with 0.05 mole (10.98 g) of zinc acetate dihydrate in 100 ml. of xylene. The mixture was heated to 140° C. for two hours. The xylene was distilled off and the residue was heated at 150° C. under nitrogen for another hour. The residue solidified when cooled to room temperature. The IR of the solid showed carbonyl absorption bands characteristic of the desired zinc carboxylate salt. Elemental analysis showed 3.72% zinc.

The procedure of Example 9(a) was repeated except that 0.05 mole (10.0 g) of cupric acetate in 100 ml. of xylene was used. The residue similarly solidified when cooled to room temperature and the IR spectrum showed absorption bands corresponding to the expected copper carboxylate salt. Elemental analysis showed 3.59% copper.

Further evaluations of power transmitting fluid compositions formulated with the ester additives prepared in the foregoing examples were carried out and are described in the following examples:

EXAMPLE 10

(a) A mineral oil fluid containing the di-ester of 2-octadecenyl succinic anhydride (OSA) with 2,2'-thio-bis-ethanol (Example 6) was evaluated in Allison C3 Friction Test; this test being a measure of the friction retention in ATF and other power transmitting fluids. The following results were obtained:

| Property | Passing Requirement | 1500 cycles | 5500 cycles |
| --- | --- | --- | --- |
| Lock-up in seconds | 0.85 max. | 0.82 | 0.85 |
| Dynamic Torque in pounds/ft | 75 min. | 104 | 82 |
| Decrease in Torque from 2500 to 5500 cycles | 30 max | | 22 |

Thus, the product of Example 1 passed this friction retention test for ATF.

(b) The oxidation inhibition of the same fluid was evaluated in the Turbo-Hydramatic Transmission Cycling Test; the acid number results being as follows:

| | Acid Number |
| --- | --- |
| Example 6 Fluid | 1.7 |
| Conventional antioxidant fluid ($C_{18}$ alkenyl succinic acid) | 11.4 |
| Maximum allowable for pass | 6.0 |

Thus, this composition passed the oxidation inhibition test used for the evaluation of ATF additives.

EXAMPLE 11

Caterpiller To-2 Test

This test measures the friction retention of a fluid used in oilcooled clutches for heavy duty equipment such as earth-moving equipment containing bronze friction material.

The test is satisfactory if, after 15,000 cycles, the increase in stopping time is 15% maximum for SAE 30, 10W-30 and 15W-40 oils, or 20% for SAE 10W oils.

To-2 Friction & Wear

A fluid containing the di-ester of Example 6 met the to-2 change in friction retention and the wear requirements.

| | TEST | LIMITS |
| --- | --- | --- |
| % INCREASE IN STOPPING TIME | | |
| TEST 1 | 18% | 20% for SAE |
| TEST 2 | 10% | 10W OIL |
| AVG. | 14% | |
| WEAR, inches | | |
| BRONZE | 0.0039 | 0.0098 |
| STEEL | 0.0022 | 0.0039 |

EXAMPLE 12—Vickers Vane Pump—Wear Performance

Here fluids containing the di-ester of Example 4 are evaluated in the Vickers Test which is important for heavy duty hydraulic fluid qualification. These data show the compositions of the present invention exhibit desirable anti-wear properties.

VICKERS 35 VQ 25 A-11

| | VICKERS 35 VQ 25 A-11 | | | |
| --- | --- | --- | --- | --- |
| | Kit No. 1 | Kit No. 2 | Kit No. 3 | Target/Kit |
| RING LOSS, mg | 30 | 40 | 10 | 75 MAX. |
| VANE LOSS, mg | 11 | 9 | 8 | 15 MAX. |
| | | | ASTM D 2882 | |
| | | WEAR | | TARGET |

| | -continued | |
|---|---|---|
| RING LOSS, mg | 35.5 | — |
| VANE LOSS, mg | 2.6 | — |
| TOTAL, mg | 38.1 | 100 |

EXAMPLE 12

FZG TEST

Several basestocks, each of which contained the diester Example 6, were evaluated in the FZG Test (a four square gear rig test). Failure load is defined as load in which scoring or seizure takes place and at which a change to high rate of wear occurs. The failure load stage target for European transmission builders (Conseil European de Coordination or CEC) is 10 minimum. This test indicates the fluids satisfy the extreme pressure requirements of fluids for heavy duty equipment use.

| | FZG |
|---|---|
| | FAILURE LOAD STAGE (MIN. 10) |
| Fluid A | 11 |
| Fluid B | 12 |
| Fluid C | 11 |
| Fluid D | 11 |
| Fluid E | 12 |

What is claimed is:

1. A process for improving the friction modification properties of a power transmission fluid containing at least one friction modification agent and a mineral oil base, which comprises employing as at least one of said friction modifying agents, at least one ester additive formed by the reaction of:
   (a) a thio bis-alkanol of the formula:

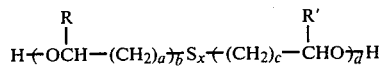

wherein R and R' each independently may be hydrogen, methyl or ethyl, x may be 1-4, and a, b, c, d, each may be independently 1-3, with (b) 1 to 2 moles, per mole of the thio-bis-alkanol, of an aliphatic hydrocarbon-substituted succinic acid or anhydride wherein the aliphatic hydrocarbon group contains from 12 to 50 carbon atoms, the additive being present in an amount effective to provide friction modification, corrosion inhibition, anti-wear, oxidation inhibition or extreme pressure properties to said fluid.

2. The process of claim 1 where there is employed from 0.05 to 2.0 weight percent of said ester in said power transmitting fluid.

3. The process according to claims 1 or 2 wherein the ester is formed by the reaction of 1 mole of said hydrocarbon succinic acid or anhydride per mole of said thio-bis-alkanol.

4. The process according to claims 1 or 2 wherein the ester is formed by the reaction of 2 moles of said hydrocaron succinic acid or anhydride per mole of said thio-bis-alkanol.

5. The process according to claims 1 or 2 wherein said ester is a mixture of mono- and di-esters.

6. The process according to claim 1 wherein said hydrocaron-substituted succinic anhydride is octadecenyl succinic anhydride.

7. The process of claims 1 or 2 wherein the thio-bis-alkanol is thiodiethanol.

8. The process of claims 1 or 2 wherein the thio-bis-alkanol is dithiodiethanol.

9. The process of claim 1 wherein there is employed from 0.1 to 0.5 wt % of said ester in said power transmitting fluid.

10. The process of claim 1 wherein said ester is borated.

* * * * *